(12) United States Patent
Kondo

(10) Patent No.: US 6,268,208 B1
(45) Date of Patent: Jul. 31, 2001

(54) DRYING CONFIGURATION AND METHOD IN SMEAR SPECIMEN PREPARATION SYSTEM

(75) Inventor: Masakazu Kondo, Kobe (JP)

(73) Assignee: Sysmex Corporation, Kobe (JP)

(*) Notice: Subject to any disclaimer, the term of this patent is extended or adjusted under 35 U.S.C. 154(b) by 0 days.

(21) Appl. No.: 09/251,459

(22) Filed: Feb. 17, 1999

(30) Foreign Application Priority Data

Feb. 18, 1998 (JP) .................................................. 10-078248

(51) Int. Cl.⁷ .............................. C12M 1/00; B01L 3/00
(52) U.S. Cl. .......................... 435/286.3; 435/286.4; 435/307.1; 435/40.51; 422/65; 422/100
(58) Field of Search ........................... 435/405, 40.51, 435/286.2, 286.3, 286.4, 287.9, 307.1, 288.3, 809; 427/2.11; 422/63, 65, 67, 99, 100, 102, 104; 118/100, 120, 415, 500

(56) References Cited

U.S. PATENT DOCUMENTS 3,995,022 * 11/1976 Heanley et al. .
4,302,480 * 11/1981 Fischer et al. .
5,779,982 * 7/1998 Aota et al. .

* cited by examiner

Primary Examiner—William H. Beisner
(74) Attorney, Agent, or Firm—Shinjyu Intellectual Property Firm

(57) ABSTRACT

In a fully automated tissue-smear preparation system, a configuration is disclosed for rapidly drying the slide smears prior to the system staining procedure. Slides bearing smeared tissue samples are briefly immersed into methyl alcohol solution, forcing liquid components in the smear cells to pass out. The smear slides are withdrawn and fanned to evaporate and dry liquid components and alcohol solution on the tissue smears. The process of drying the smear slides is accordingly optimized for the subsequent staining procedure.

11 Claims, 3 Drawing Sheets

DRYING CONFIGURATION AND METHOD IN SMEAR SPECIMEN PREPARATION SYSTEM

BACKGROUND OF THE INVENTION

1. Technical Field

The present invention relates to a specimen preparation system and associated method for preparing blood-cell smears or the like for examination; in particular the invention relates to time-reduction improvement in the drying process part of a smear specimen preparation procedure carried out by the system prior to staining the specimens.

2. Description of Related Art

An example of a smear specimen preparation apparatus in which the processes from smearing blood onto glass slides to staining are automated is disclosed in Japanese Laid-Open Pat. Publ. No. 8-271390. This apparatus uses cassettes for housing glass slides and solutions, smears blood on the glass slides to prepare smear specimens, stores the smear specimens into empty cassettes that are sent in one by one, and dispenses staining solutions into the cassettes to stain the blood cells.

To prepare neat, stably stained specimens, the smears on the glass slides must be sufficiently dried before staining. If there is no concern with process time, the specimens may be dried naturally for some length of time, for example, from one to a few hours. Toward raising processing speed, however, it is necessary to shorten the time for the drying procedure, which is prior to staining.

There is one method, for example, in which the specimens are cool-air dried in air blown by a fan. However, changes in the surrounding environment give rise somewhat to variations in the drying conditions (in hot or humid situations, insufficient drying is likely). Inconsistencies in the drying conditions will appear as inconsistencies in the staining conditions, which ultimately will affect the outcome of the stained specimens. Carrying out the staining process on an insufficiently dried smear specimen leads to unsatisfactorily stained, unclear specimens.

Sir John V. Dacie and S. M. Lewis describe a rapid staining method on pp. 54–55 of *Practical Haematology*, Sixth Edition (Churchill Livingstone, London, 1984). Nevertheless, what they note is related not to shortening drying procedure time, but rather to shortening the time for the subsequent staining procedure.

SUMMARY OF THE INVENTION

Accordingly, it is an object of the present invention to shorten the time interval in which smear specimens are dried in a system and associated method for preparing smear specimens, thereby enabling satisfactory staining results in the subsequent staining process.

In a smear preparation system of the present invention, the following procedures are carried out by corresponding devices of the system: 1) a smearing procedure wherein subject particles for examination are smeared onto an element for smear specimens; 2) a drying procedure wherein, after the smear specimen—the element for smear specimens onto which the subject particles for examination have been smeared—is contacted with alcohol, the liquid present on the smear specimen is evaporated and dried; and 3) a staining procedure wherein the particles on the subject smear specimen for examination are stained.

Important to the present invention is the distinction between drying and fixing in the preparation of subject smear samples for examination. Drying removes water from smear cells to prepare them osmotically to accept the stain. In other words, dehydration makes the cells hypertonic with respect to the stain solution. Fixing preserves tissue morphology and molecular composition.

The staining procedure includes fixing, staining and rinsing processes. For example, one process of the staining procedure is to immerse a smear specimen into methyl alcohol or May-Grünwald solution, which contains methyl alcohol at high concentration. Because this is a fixing process in the staining procedure, however, the sample is normally immersed 2 or 3 minutes or more.

In contrast, contacting with alcohol in the present invention is for a far shorter interval. Moreover, because the liquid component on the smear specimen is evaporated and dried, the effect on the cells is different from that noted above. Accordingly, the present invention is a means for solving the problem of inconsistencies in the pre-staining drying process.

"Short interval" herein means an extent of time that does not lead to the cells subject to observation becoming fixed. Further, "short interval" signifies 30 seconds or less, preferably 10 seconds or less.

Although the dehydration mechanism of cells is not altogether precisely understood, the present invention arose through trial and error, and is based on the finding that if a smear specimen is briefly contacted with methyl alcohol, and the liquid component on the smear specimen is soon evaporated and dried, in the succeeding staining process stabilized suitable results are obtained.

It is probable that the alcohol, in particular short-chain alcohol, increases osmotic pressure external to the cells, thereby dehydrating them. Accordingly, "liquid component on the smear specimen" herein signifies alcohol or alcohol in solution, together with water content that has passed from the smear cells.

In an apparatus for preparing smear specimens that stains subject cells for observation by immersing the smear specimens, which are substrates for smear specimens onto which subject cells for observation have been smeared, into a staining solution, a smear specimen preparation system of the present invention is characterized in being fitted with a smear specimen drying mechanism that, at the earlier phase portion of the above-noted staining process, immerses the smear specimen into alcohol and then evaporates and dries the liquid component on the smear specimen.

From an automation standpoint, the smear specimen preparation apparatus preferably is furnished with cassettes for housing the smear specimens; a conveyance section for conveying the cassettes; a stowing section for stowing the smear specimens into the cassettes; and a staining section that dispenses staining solution into the cassettes to stain the subject cells on the smear specimen for observation. Herein, the staining solution is dispensed into the cassettes and the smear specimens are thus stained within the cassettes. The present invention employs these cassettes for carrying out drying of the smear specimens prior to staining.

Accordingly, a smear specimen drying method of the present invention makes it possible to dry smear specimens in a short time interval to be in suitable condition for staining.

By applying this technique to an automated smear specimen preparation apparatus, smear specimens in satisfactory condition for staining can be stably obtained, without requiring much time for drying and irrespective of changes in temperature, humidity and like environmental conditions.

The foregoing and other objects, features, aspects and advantages of the present invention will become more apparent from the following detailed description in conjunction with the accompanying drawings.

DETAILED DESCRIPTION OF THE PREFERRED EMBODIMENTS

Figure 1:
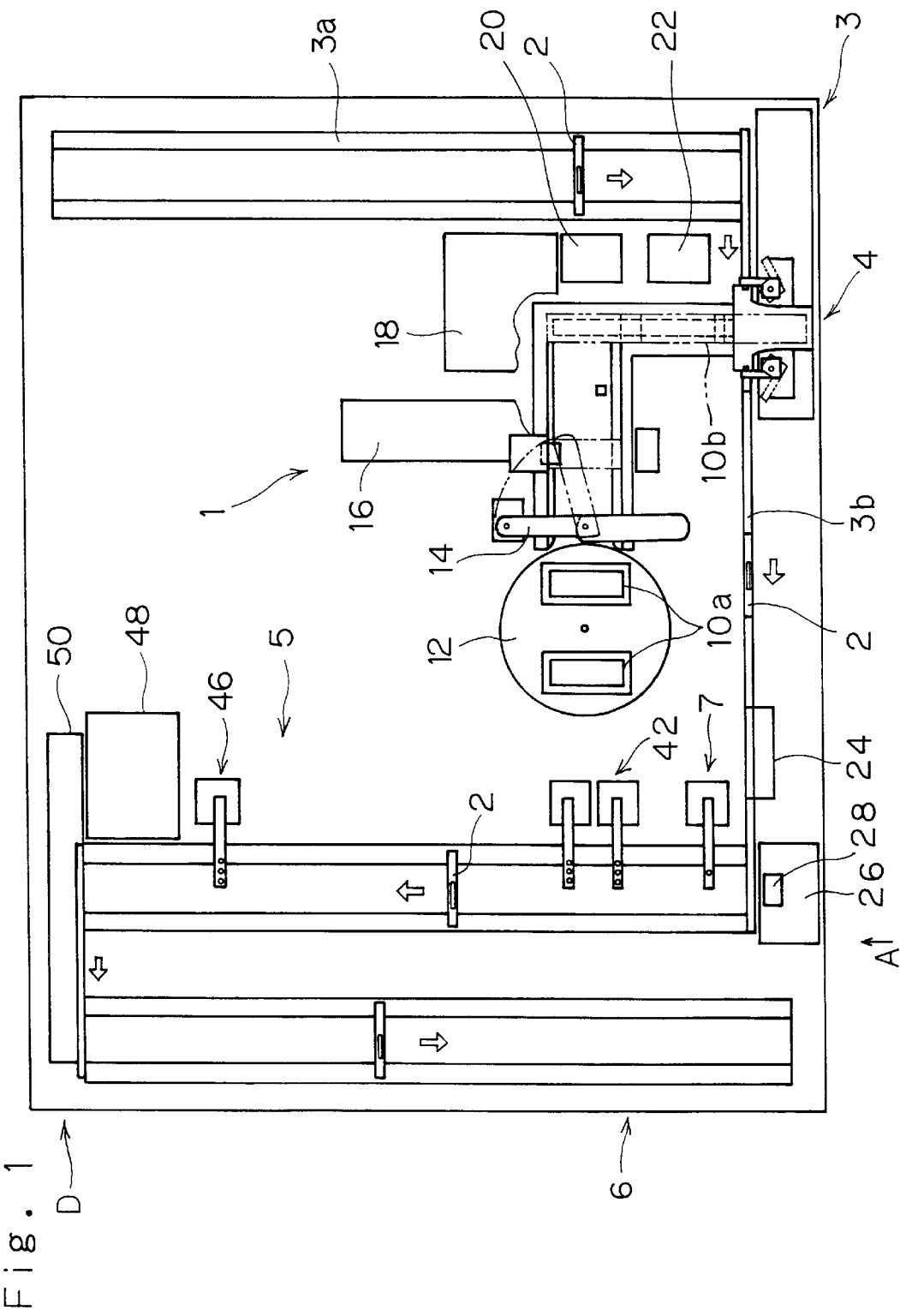
FIG. 1 is a schematic plan view illustrating an apparatus in a system for preparing smear specimens according to the present invention.
Figure 2:
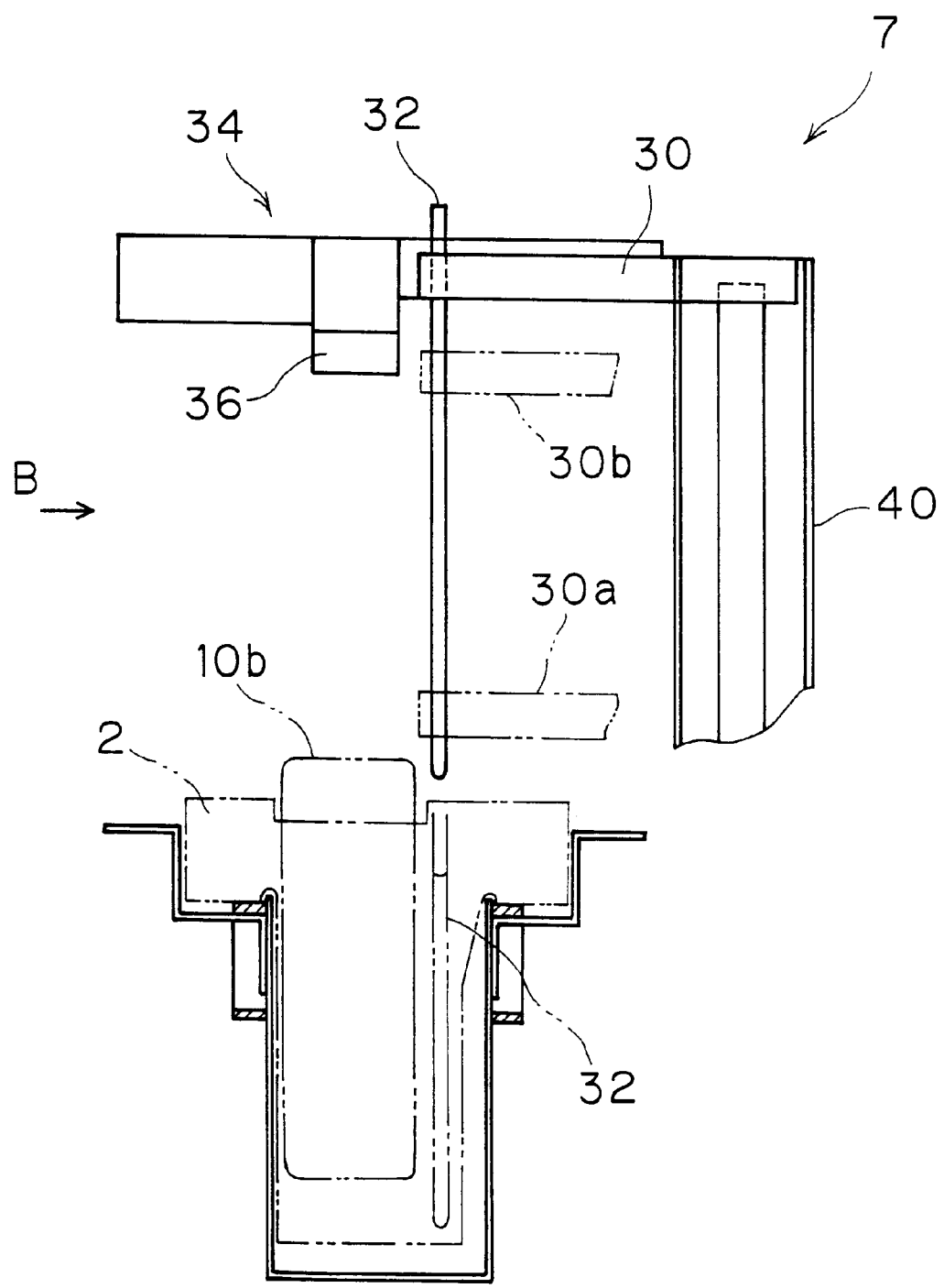
FIG. 2 is a fragmentary elevational view seen in the direction of arrow A in FIG. 1, illustrating an example of a smear specimen drying mechanism in the present invention.
Figure 3:
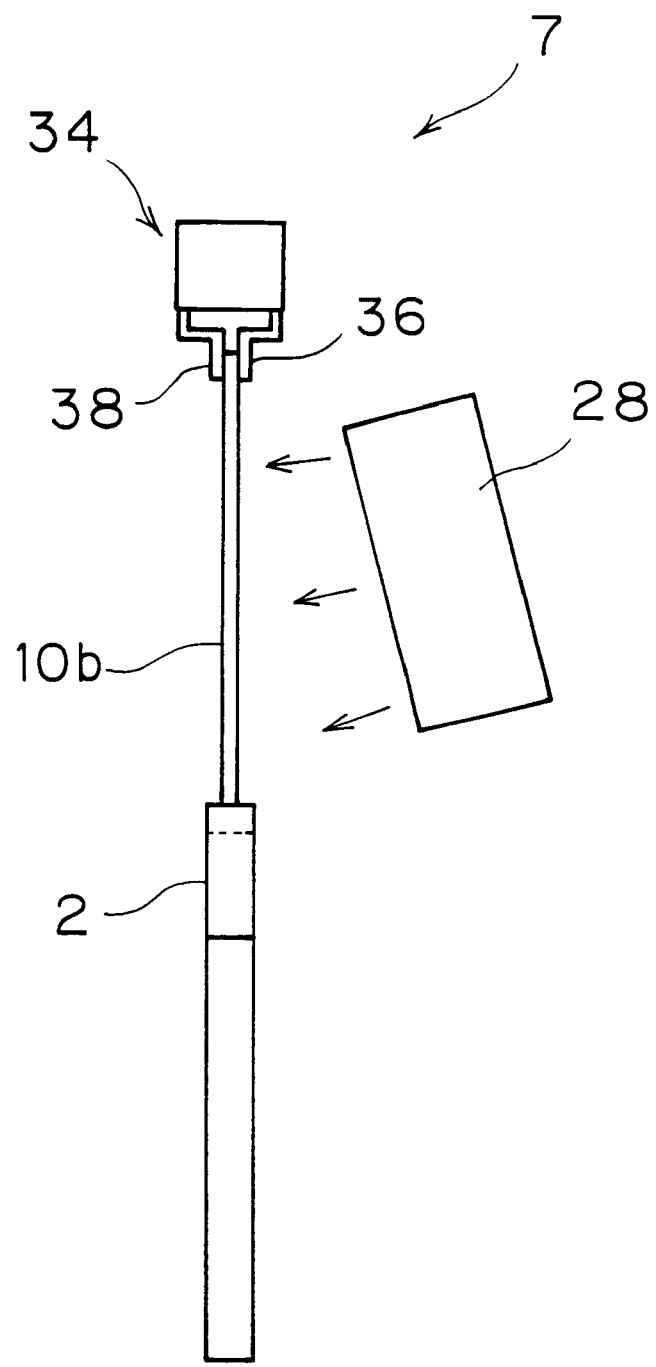
FIG. 3 is a lateral view, seen in the direction of arrow B in FIG. 2, of a principal section of the smear specimen drying mechanism wherein a glass slide is being held.

Glass slides for microscopes are generally used as smear specimen a substrate onto which subject cells for observation are smeared. The present invention is nonetheless applicable to substrates of material or form different from glass slides.

To contact the smear specimens with alcohol, alcohol can be directly sprayed or dropped on to the smear specimens. Experiments have shown, however, that a method wherein smear specimens are immersed gently into alcohol and gently pulled up was most suitable (the specimens stained well in the staining process). The smear specimens may be immersed into alcohol slide by slide, or simultaneously as a plurality.

A short interval of 30 seconds or less, preferably 10 seconds or less, is a sufficient period for contacting with alcohol. If the alcohol contacting time is, for example, one minute or more, the cells will start to become fixed, such that it would not make sense to carry out the present drying process. Further, too short an interval makes the effects of the present drying process unsatisfactory; therefore the contacting with alcohol period is more preferably between 2 and 10 seconds, more preferably still between 2 and 8 seconds.

The evaporating and drying processes carried out after contacting with alcohol may be natural evaporative drying, however, if more rapid drying is desired, evaporation and drying may be conducted by fanning the specimens for about 5 to 10 seconds.

Herein, alcohol means a solution of high alcohol concentration, and methyl alcohol having a concentration of over 95% is useable. Not only pure methyl alcohol is usable, but also solutions containing other materials with methyl alcohol as the chief constituent. For instance, Wright's solution or May-Grünwald solution can be substituted.

A configuration as a smear specimen drying mechanism for the present smear specimen drying technique comprises a dispensing means for dispensing alcohol into slide housing cassettes and a retaining means for holding and vertically shifting smear specimens. More specifically, the configuration can comprise a vertically shifting arm section, a nozzle section for dispensing alcohol into the cassettes, and a clasper attached to the arm section for clasping the smear specimens.

The nozzle section may comprise nozzle elements solely for dispensing and nozzle elements solely for discharging, or may comprise nozzle elements serving both functions.

In addition, from the viewpoint of drying time reduction, the drying configuration preferably is furnished with a fanning means for blowing air onto smear specimens clasped by the clasping section and pulled up from the cassettes.

Description will now be given of operation of the smeared sample drying mechanism. First, the arm descends and the retaining means clasps a smear specimen stored in a cassette. The arm then ascends and the smear specimen is pulled up from the cassette. Alcohol is dispensed into the cassette from the nozzle section. The arm descends, returning the smear specimen into the cassette and immersing it into the alcohol. (To reduce the time to this point in the procedure, the present invention can be embodied in a form in which alcohol is dispensed into cassettes wherein the smear specimens are housed.)

After immersion in alcohol for a few seconds, the arm ascends and the smear specimen is pulled up from the cassette. Air is then blown by the fanning means onto the smear specimens to evaporate and dry the liquid component, thereby obtaining smear specimens suitable for staining.

Subsequently, the arm descends and the drying-processed smear specimen is returned into the cassette, whereupon the staining procedure is begun. Wherein the alcohol solution is essentially alcohol only, it is discharged from the cassette, after which solution(s) for the staining process are dispensed into the cassette.

Embodiment

Reference is now made to FIG. 1, a schematic plan view of a smear specimen preparation apparatus D in which a smear drying configuration of the present invention is adapted. The apparatus D comprises a smearing section 1 for smearing blood onto a glass slide 10*a*; a cassette 2 for housing the glass slides 10*a*; a conveyance section 3 (3*a*, 3*b*) for removably setting and conveying the cassette 2; a housing operation section 4 for storing the glass slide smears 10*b* slide by slide into the cassette 2; a staining section 5 that performs staining after a staining solution is supplied to the cassette 2 containing the glass slide smears; and a storage section 6 that stores the cassettes 2 housing the stained slides.

In the smearing section 1, glass slides 10*a* are taken out one by one from a turntable 12 into which a plurality of slides is set. Then in a first predetermined location, blood is dripped onto the slides 10*a* in succession by a blood dispensing mechanism 14, and then smeared by a smearing mechanism 16. In a second predetermined location, sample number and similarly necessary information is printed onto a frosted portion of the blood-smeared slides 10*b* by a printer 18. In third and fourth positions, the smeared slides 10*b* are then cool-air dried by fans 20 and 22.

Subsequently, an empty cassette 2 is fed by the conveyance part 3*a*. The blood-smeared glass slides 10*b* are stored individually into the empty cassette 2 by the housing operation section 4. Thereafter, the cassette 2 is conveyed by the conveyance section 3*b* and sent to the staining section 5 by a sending mechanism 26. Herein, the time from blood smearing to arrival at the staining section 5 is 30 seconds.

Reference numeral 24 designates a cassette interrupt-supply section that is provided so that cassettes housing slide smears to be submitted to the staining process can be supplied in interrupt fashion into the conveyance line, separate from cassette conveyance by the conveyance section 3*b*.

Disposed on the front portion of the staining section 5 is a smear specimen drying mechanism 7 that performs drying of smeared slides in a short time interval.

One end of an arm 30 extending horizontally is attached to a shaft 40 and is slid up and down by a motor (not shown), wherein the arm 30 reciprocates vertically. To the other end of the arm 30, there are attached a nozzle 32 for dispensing May-Grünwald solution and a clasper 34 for clasping a smeared slide 10b.

The May-Grünwald solution comprises mainly methanol (about 99%).

The clasper 34 is constituted to employ a pneumatic device popularly known as an "air hand," for clasping objects by narrowing the gap between two clasping pieces 36 and 38 by means of an air supply. The inside face of the one holding piece 36, which is brought into contact with the frosted portion of the glass slide 10b, is fitted with a non-slip soft material (such as a rubber material or vinyl chloride sheet). The inside face of the other holding piece 38 is provided with a plurality of fine scores (grooves), in order to prevent adherence to the glass slide 10b.

Operation of the smear specimen drying mechanism 7 will be described in detail.

A cassette 2 fed to staining section 5 is brought to a stop at a location below the smear specimen drying mechanism 7. For this, a pin (not shown) projecting through the front of the cassette 2 is provided to stop the cassette 2 in a predetermined position. With the cassette 2 standing at rest, the smear specimens are dried by the following operations [1]–[7].

[1] Arm Lowered

The arm 30 is lowered from the uppermost position (30) to the lowermost position (30a).

[2] Slide Clasped

The clasper 34 is operated to clasp the glass slide 10b.

[3] Slide Raised

The arm 30 is raised to an intermediate point (30b) to lift the glass slide 10b.

[4] Alcohol Dispensing

Nozzle 32 dispenses 6 ml of alcohol (herein, May-Grünwald solution) into cassette 2.

[5] Slide Immersion

The arm 30 is lowered to the lowermost position to immerse the glass slide 10b into the alcohol (May-Grünwald solution). The slide 10b is left thus for a predetermined time (which can be arbitrarily set between 1 and 60 seconds; herein 5 seconds).

[6] Slide Raised

The arm 30 is raised to the intermediate point to lift the glass slide 10b.

[7] Evaporation and Drying by Fanning

A fan 28 is run for a predetermined time (which can be arbitrarily set between 1 and 60 seconds; 5 seconds herein) to blow air against the smeared surface of the glass slide 10b to evaporate and dry liquid components on the surface of smear. Through steps [1] to [7], the drying process is completed.

Subsequently, a staining process (herein, the May-Grünwald-Giemsa double stain) is performed. The staining process is described in [8]–[11] below. The staining process carried out is likewise as is conventional.

[8] Immersion into May-Grünwald Solution

The arm 30 is lowered to the lowermost position to immerse the glass slide 10b again into the May-Grünwald solution. Upon immersion, the May-Grünwald-Giemsa double staining process is started. That is, the clasper 34 releases the glass slide 10b, and the arm 30 is raised to the uppermost position. The cassette 2 is immersed into the May-Grünwald solution for a predetermined time (which can be set to between 1 and 5 minutes) as a staining process while it is conveyed.

[9] Immersion into May-Grünwald Diluent

In a suction exhausting device 42, the May-Grünwald solution in the cassette 2 is discharged, and next May-Grünwald diluent is dispensed into the cassette 2. The cassette 2 is immersed into the May-Grünwald diluent for a predetermined time (which can be set to between 1 and 5 minutes) while it is conveyed.

[10] Immersion into Giemsa Solution

In the suction exhausting device 44, the May-Grünwald diluent in the cassette 2 is discharged, and next Giemsa solution is dispensed into the cassette 2. The cassette 2 is immersed into the Giemsa solution for a predetermined time (which can be set to between 1 and 5 minutes) while it is conveyed.

[11] Washing

In a suction exhausting device 46, the Giemsa solution in the cassette 2 is discharged, and wash water is dispensed into and discharged from the cassette 2 to wash the glass slide 10b.

[12] Fan Drying

A fan 48 blows air against the stained and washed glass slide 10b to dry it.

[13] Storage

The cassettes 2 containing stained glass slides 10b is fed sequentially by a feed mechanism 50 to a storage section 6 for stocking and storage.

An operator takes out the cassettes 2 from the storage section 6, and sets a glass slide 10b into a microscope in order to observe the blood cells.

Various details of the present invention may be changed without departing from its spirit nor its scope. Furthermore, the foregoing description of the embodiments according to the present invention are provided for illustration only, and not for the purpose of limiting the invention as defined by the appended claims and their equivalents.

What is claimed is:

1. In a smear specimen preparation apparatus having a smearing section for smearing onto substrates tissue cells for observation, and a staining section for staining the smeared substrates by immersion into a staining solution to stain the cells, a smear specimen drying system comprising:

cassettes for housing smeared substrates prepared as smear specimens in the smearing section;

a housing operation section for storing said smear specimens into said cassettes;

a conveyance section for conveying said cassettes between said housing operation section and said staining section; and a smear specimen drying mechanism disposed after said housing operation section and before said staining section, said smear specimen drying mechanism including an alcohol dispensing means for dispensing alcohol into said cassettes as conveyed to said smear specimen drying mechanism by said conveyance section, and a reciprocative retaining means for holding and vertically shifting said smear specimens into and out of said cassettes to contact said smear specimens with alcohol for an interval sufficient to dehydrate the smear cells, but less than onset of fixing of the smear tissue.

2. A smear specimen drying system as set forth in claim 1, wherein the period of time in which the smear specimen is contacted with alcohol in said smear specimen drying mechanism is not more than 10 seconds.

3. A smear specimen drying system as set forth in claim 1, wherein said smear specimen drying mechanism further comprises a fan disposed adjacent said reciprocative retaining means, for blowing air against the smear specimen contacted with alcohol so as to evaporate and dry liquid components on the smear specimen.

4. A smear specimen drying system as set forth in claim 1, wherein said reciprocative retaining means comprises:

a vertically reciprocative arm member; and a clasping member attached to said arm member for clasping the smear specimens, wherein
said alcohol dispensing means comprises a nozzle section disposed on said arm member for dispensing alcohol into the cassettes.

5. A smear specimen preparation apparatus as set forth in claim 1, wherein the alcohol contains a stain.

6. A method of employing the smear specimen drying system as set forth in claim 1, the method comprising the steps of:

operating said reciprocative retaining means to shift said smear specimens vertically into said cassettes to alcohol-contact said smear specimens with one of alcohol and an alcohol solution for an interval sufficient to dehydrate the smear cells, but less than the onset of fixing of the subject tissue, and operating said reciprocative retaining means to shift said smear specimens vertically out of said cassettes to remove said smear specimens from contact with alcohol; and holding said smear specimens out of said cassettes to evaporate and dry liquid components on the smear specimen.

7. The method as set forth in claim 6, wherein in said step of alcohol-contacting the smear specimen, the alcohol contact interval is not more than 30 seconds.

8. The method as set forth in claim 7, wherein in said step of alcohol-contacting the smear specimen, the alcohol contact interval is approximately 2 to 5 seconds.

9. The method as set forth in claim 6, wherein said step of evaporating and drying liquid components on the smear specimen includes the sub-step of operating said fan to blow air against the smear specimen contacted with one of alcohol and an alcohol solution.

10. The method as set forth in claim 6, wherein in said step of alcohol-contacting the smear specimen, the smear specimen is contacted with an alcohol solution containing at least 95% methyl alcohol.

11. The method as set forth in claim 10, wherein the alcohol solution containing at least 95% methyl alcohol is one of May-Grünwald solution and Wright's solution.

* * * * *